(12) United States Patent
Manning

(10) Patent No.: US 6,298,852 B1
(45) Date of Patent: Oct. 9, 2001

(54) EXTENSION CONDOM WITH MEANS OF ABSORPTION

(75) Inventor: Eric K. Manning, 1615 Stacey Ct., Richardson, TX (US) 75081

(73) Assignee: Eric K. Manning, Dallas, TX (US)

( * ) Notice: Subject to any disclaimer, the term of this patent is extended or adjusted under 35 U.S.C. 154(b) by 0 days.

(21) Appl. No.: 09/262,654

(22) Filed: Mar. 4, 1999

(51) Int. Cl.$^7$ .......................................... A61F 6/04
(52) U.S. Cl. ........................................ 128/844; 128/918
(58) Field of Search .................. 128/842, 844, 128/918; 604/347–353

(56) References Cited

U.S. PATENT DOCUMENTS

| | | | |
|---|---|---|---|
| 3,648,700 | * 3/1972 | Warner | 128/844 |
| 4,840,188 | * 6/1989 | Heidenfelder | 128/844 |
| 4,972,849 | * 11/1990 | Park | 128/842 |
| 5,113,873 | * 5/1992 | Boarman | 128/844 |
| 5,325,871 | * 7/1994 | Reddy | 128/844 |

* cited by examiner

Primary Examiner—Michael A. Brown
(74) Attorney, Agent, or Firm—Eric K. Manning

(57) ABSTRACT

An improved condom improving the size of the male penis, improved sensation for the female, preventing leakage and transfer of semen. The extension condom with means of absorption includes a traditional condom, and a sponge which works simultaneously to prevent the transfer of micro-organisms between sex partners. The sponge (along with other porous, and non-porous materials) can also be used to extend the size of the penis.

18 Claims, 1 Drawing Sheet

EXTENSION CONDOM WITH MEANS OF ABSORPTION

FIELD OF THE INVENTION

This invention relates to birth control devices and, more particularly, to an improved condom having a penis extension and means of absorption.

BACKGROUND OF THE INVENTION

Condoms have been used as a form of birth control and protection from sexually transmitted diseases for many years. The condom is a thin protective sheath for the penis used to prevent venereal infection or as a contraceptive. The condom forms a sheath around a shaft of a penis. The condom is typically made from a non-porous material preventing the transfer of semen to a woman, and, in most cases, prevents pregnancy. Materials include synthetic rubbers, latex and sheepskin.

However, there are disadvantages to using condoms during sexual intercourse. Since the condom fits over the entire length of the penis, a significant reduction in sensation is noticed by the man during sexual intercourse. Another disadvantage is that, on numerous occasions, the condom can slip towards the top of the penis during the act of intercourse, causing the leakage of semen from the base of the condom. The constriction band used to hold a condom in place on the penis is typically located at the base of the condom. Since the constriction band has only the base to grasp, the condom can slip or slide during movement associated with sexual intercourse. This could allow the transfer of semen from a man to the women.

Thus, it would be a distinct advantage to have an improved condom which provides increased sensation during sexual intercourse. Additionally, it would be advantageous to have an improved condom which does not leak, and prevent the transfer of semen during intercourse. It is an object of the present invention to provide such an improved condom.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF THE INVENTION

The present invention is an improved condom providing improved sensation for the female during sexual intercourse, also preventing leakage and transfer of semen.

Figure 1:
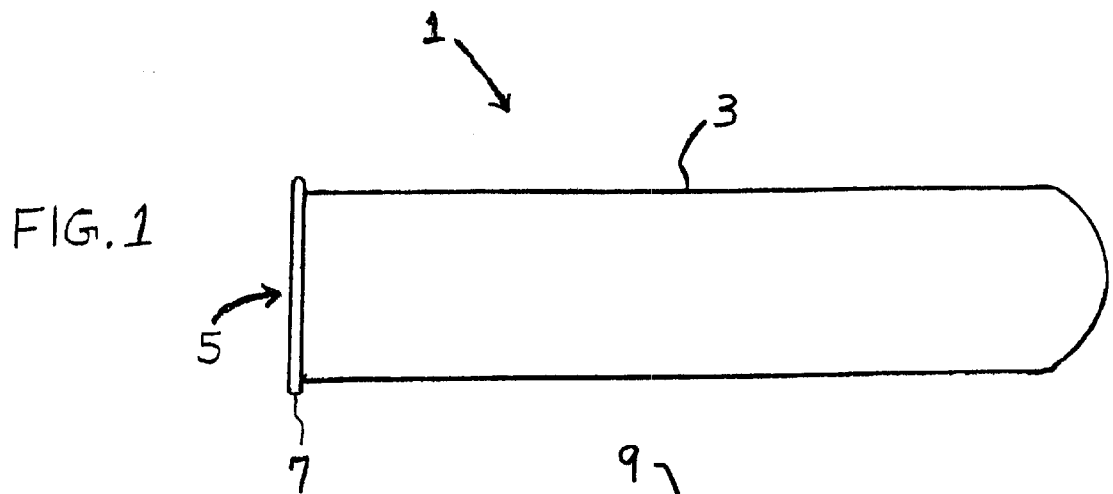
FIG. 1 is a perspective view illustrating a traditional condom.

FIG. 1 is a perspective view illustrating a traditional condom 1. The traditional condom 1 includes a main body 3, an opening 5, and a elastomeric band 7. The entire traditional condom 1 is made of a non-porous material (e.g., rubber, latex, polyurethane, or lambskin) preventing the transmission of semen during intercourse. The main body 3 is tube-shaped for covering a entire penis.

At the base of the main body 3 is the circular opening 5. Surrounding the opening 5 is the elastomeric band 7. The elastomeric band 7 is an annular restricting band made of an elastomeric material for firmly grasping the penis for the purpose of holding the condom in place on the penis.

Figure 2:
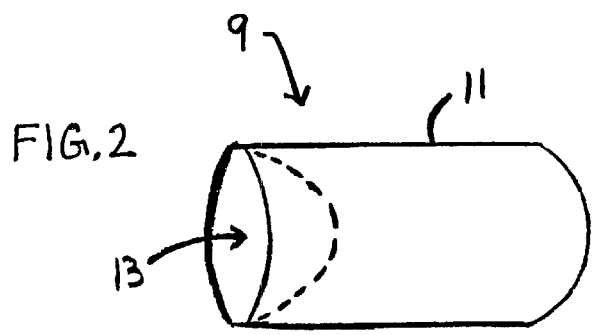
FIG. 2 is a perspective view illustrating a penis extension.

FIG. 2 is a perspective view illustrating the penis extension 9, includes a main body 11, and a opening 13.

The main body 11 is made of porous, non-porous, and or manufactured from solid and absorbent materials either singularly and in combination with such materials as sponges (soft and hard), cloth, synthetic cloth, cotton, plastic, plastic composites, rubber, latex, polyurethane, epidermal tissue, and skin. The penis extension 9, may also be bactericidal, hypoallergenic, mycocidal, spermicidal, and viralcidal.

At the base of the main body 11, is the circular opening 13. The opening 13 is half-moon shaped to surround the tip of the penis, to prevent any bends between the penis, and the main body 11.

Figure 4:
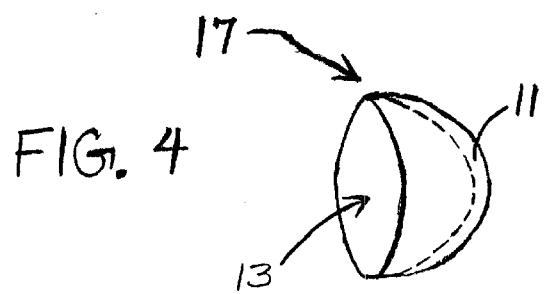
FIG. 4 is a perspective view illustrating a round penis extension.

The main body 11 is tube-shaped for extending the shaft of the penis (for pleasure purposes), with size from 0.1–6 inches either in length, width, or diameter. The main body 11 may also be round (as seen in FIG. 4), or oblong. The length of the main body 11 may very depending on preference, and or materials used to manufacture.

Figure 3:
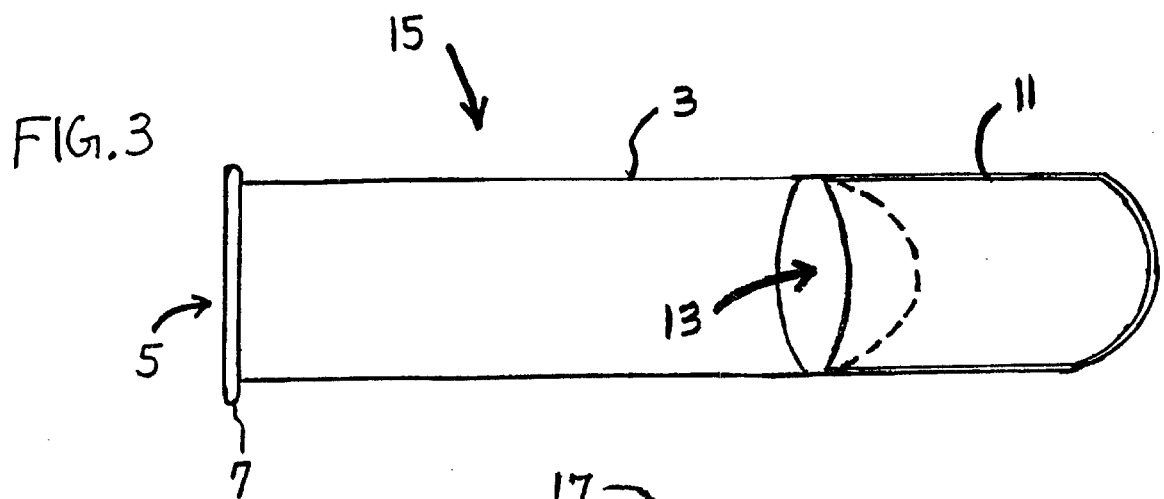
FIG. 3 is a side view of a penis extension inside a traditional condom.

FIG. 3 is a side view of a penis extension 9, inside a traditional condom 1, thereby creating the extension condom 15. The extension condom 15, includes the main body 11 (as seen in FIGS. 2, 4), a main body 3 (as seen in FIG. 1) in which a mandrel is configured to manufacture the main body 3, in which it will be able to encompass a penis and a penis extension 9. The main body 3, are from a group of singularly or in combination, consisting of rubber, latex, polyurethane, plastic, and plastic composites. The extension condom 15, includes a opening 13 (as seen in FIG. 2 & FIG. 4), a opening 5 (as seen in FIG. 1), and a elastomeric band 7 (as seen in FIG. 1).

The elastomeric band 7 firmly grasps the penis for the purpose of holding the penis extension 9, and the main body 3 (condom) firmly in place.

During sexual intercourse the penis extension 9 extends the shaft of the penis, also functioning as a means of absorption, and thus preventing the transfer of fluid during sexual intercourse.

The penis extension 9, may also be bonded or attached to the main body 3, by glue or adhesive, whereas the adhesive is bactericidal, hypoallergenic, mycocidal, spermicidal, and viralcidal. The adhesive is also manufactured from totally organic substances.

It is therefore contemplated that one skilled in the art could, manufacture the numerous modifications and variations of the components, dimensions and parameters described above without departing from the spirit and scope of this invention.

FIG. 4 is a perspeective view illustration of a round penis extension 17. FIG. 4 is a example of FIG. 2, in it's round shape. FIG. 4 has all the make-up and functions of FIG. 2 (e.g., FIG. 2).

What is claimed is:

1. An improved condom comprising a condom having a tubular body and a penis extension for extending the length of the tubular body, an elastomeric band attached to the tubular body at an open end of said condom, said penis extension having a half-moon shape at one end to allow said penis extension to surround the tip of the penis and prevent bends between the penis and said penis extension.

2. The improved condom of claim 1, wherein the penis extension is porous and approximately 0.1–6 inches in diameter.

3. The improved condom of claim 2, wherein the condom is made of an absorbent material.

4. The improved condom of claim 2, wherein the penis extension is made from a solid material.

5. The improved condom of claim 1, wherein the penis extension is non-porus and approximately 0.1–6 inches in diameter.

6. The improved condom of claim 1, wherein the penis extension is formed from a group consisting of a sponge, cloth, cotton, synthetic cloth, plastic compositions, rubber, latex, polyurethane, epidermal tissue, endodermal tissue, smooth muscles tissue or skin.

7. The improved condom of claim 6, wherein the penis extension is boned to the condom by glue.

8. The improved condom of claim 6, wherein the penis extension is boned to the condom by adhesive.

9. The improved condom of claim 8, wherein the adhesive is viralcidal.

10. The improved condom of claim 8, wherein the adhesive is bactericidal.

11. The improved condom of claim 8, wherein the adhesive is spermicidal.

12. The improved condom of claim 8, wherein the adhesive is an organic substance.

13. The improved condom of claims 6, wherein the penis extension is viralcidal.

14. The improved condom of claim 6, wherein the penis extension is bactericidal.

15. The improved condom of claim 6, wherein the penis extension is mycocidal.

16. The improved condom of claim 6, wherein the penis extension is hypoallergenic.

17. The improved condom of claim 6, wherein the penis extension is spermicidal.

18. The improved condom of claim 1, wherein the condom is formed from a group consisting of rubber, latex, polyurethane, plastic or a plastic composition.

* * * * *